United States Patent [19]

Saitoh

[11] Patent Number: 4,978,534

[45] Date of Patent: Dec. 18, 1990

[54] GABEXATE MESYLATE OINTMENT

[76] Inventor: Kazuo Saitoh, 14, 799-banchi, Kanegatani, Asahi-ku, Yokohama-shi, Kanagawa, Japan

[21] Appl. No.: 281,145

[22] Filed: Dec. 6, 1988

[30] Foreign Application Priority Data

Dec. 12, 1987 [JP] Japan .................... 62-314958

[51] Int. Cl.$^5$ ................................ A61K 9/14
[52] U.S. Cl. .................... 424/484; 424/435; 424/487
[58] Field of Search .............. 424/484, 487, 435

[56] References Cited

U.S. PATENT DOCUMENTS 4,572,832 2/1986 Kigasawa et al. ............ 424/435
4,777,033 10/1988 Ikura et al. .................... 424/487

Primary Examiner—Thurman K. Page
Assistant Examiner—P. L. Prater
Attorney, Agent, or Firm—Edwin E. Greigg

[57] ABSTRACT

A gabexate mesylate ointment according to the present invention comprises 0.01-8% by weight of gabexate mesylate, 25-80% by weight of white vaseline, and 20-75% by weight of at least one type of viscosity controller selected from the group consisting of liquid parrafin, squalene and fatty acid ester containing 8-20 carbon atoms. Where desirable, this ointment is added with 1-20% by weight of at least one type of viscosity controlling auxiliary selected from the group consisting of higher alcohol and higher fatty acid containing 14-34 carbon atoms, beeswax and spermaceti wax.

26 Claims, No Drawings

GABEXATE MESYLATE OINTMENT

BACKGROUND OF THE INVENTION (1) Field of the Invention

The present invention relates to gabexate mesylate ointments which have no harmful effect such as stimulation or allergic development on the skin or mucosa, i.e. have a high degree of skin safety, and which contain gabexate mesylate with improved stability in an ointment base.

(2) Description of the Prior Art

Gabexate mesylate is a compound expressed in the following structural formula:

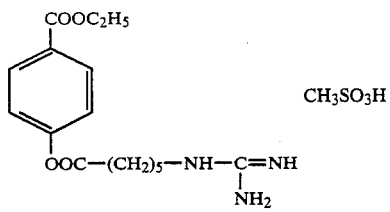

It has a function to deactivate proteolytic enzyme (hereinafter referred to as protease), and is dissolved in a fructose solution or the like to be instilled for treating pancreatitis.

Gabexate mesylate has been used in recent years as ointment for preventing inflammation, erosion and ulceration of the skin, mucosa or tissue adjacent outlet positions of alimentary canal fistulas including an artificial anus.

Where there is trouble with the pancreas or the alimentary canal, it is sometimes necessary to directly discharge pancreatic juice and other digestive fluids and contents of the alimentary canal from the body (the abdomen). This is done through a so-called alimentary canal fistula.

Pancreatic juice contains protease to decompose protein present in foods in the alimentary canal but not to digest the alimentary canal per se.

At the outlet position of a fistula, however, the contents of the alimentary canal leak out and adhere to the skin at times, and the digestive fluids tend to contact the skin. As a result, body surfaces, particularly the skin, mucosa and tissue adjacent the outlet position of the fistula can be digested or eroded by the protein-decomposing function of protease. This leads to dermatitis, erosion or ulceration, and in serious cases to peritonitis.

Among the alimentary canal fistulas, pancreatic and small-intestinal fistulas are most vulnerable to the action of protease. Apart from these, not only a fistula connected to an upper part of the large intestine but a fistula (or an artificial anus) connected to a lower part thereof is subjected to the influence of protease which has not lost its activity. Where such a fistula must be used over a long period or for life, dermitis, erosion or an ulcer will develop on abdominal skin, mucosa or tissue.

From this point of view, gabexate mesylate which is a protease-deactivating substance is used for preventing decomposition of protein in abdominal surfaces. Excellent results are obtained by applying a gabexate mesylate ointment to positions adjacent the outlet of an alimentary canal fistula.

Other types of inflammation also result from the action of protease. The gabexate mesylate ointment is therefore used in the treatment of a trauma, in a postoperative treatment, and in the treatment of dermitis, erosion or an ulcer, or applied to a position of skin trouble where mucosa is exposed and an exudate is present. The gabexate mesylate ointment thus applied is known to produce excellent results by suppressing the activity of protease and thereby mitigating the traumatic pain.

While gabexate mesylate is very effective in the treatment of various troubles, this substance is extremely unstable and readily becomes decomposed when heated. The decomposition is greatly expedited particularly in the presence of moisture, such as in humid atmosphere.

There is thus a problem in long-term stability (storage life) of the gabexate mesylate ointment having gabexate mesylate contained in the ointment base. For this reason the gabexate mesylate ointment is not commercially available. Currently the gabexate mesylate ointment is prepared according to prescriptions as necessary in hospital dispensaries or the like.

The ointment is prepared by using gabexate mesylate intended for injection purposes (with 100 mg of gabexate mesylate and 200 mg of an excipient in 1 vial). The ointment base often consists of Macrogol Ointment, boric acid and zinc oxide ointment, or Azunol Ointment (manufactured by Nippon Shinyaku Co., Ltd., Japan).

This gabexate mesylate ointment must be prepared according prescriptions in hospital dispensaries every now and again, which is very troublesome. Moreover, the gabexate mesylate ointment prepared as prescribed becomes decomposed during a use period and loses efficacy as days pass since no improvement has been made in the stability of gabexate mesylate in the ointment base.

There are Macrogol ointments of various molecular weights, and they may be mixed to form an ointment base having a viscosity suitable for intended purposes. On the other hand, this ointment base which is water-soluble is a main cause of the gabexate mesylate instability.

Attempts have been made recently to improve the stability of gabexate mesylate in the ointment base by adding ferric chloride to the Macrogol ointment base. It has been reported that an addition in 0.01% by weight of ferric chloride is effective to maintain stability at a storage temperature of 30° C. for 6 months.

However, the Macrogol base used in the gabexate mesylate ointment is not suited for use from the point of view of skin stimulation and skin allergy. The addition of ferric chloride doubles stimulation of the body part to which the ointment is applied, especially mucosa, which poses a problem in the safety aspect.

The Macrogol ointment base is hydrophilic, and the ointment is not expected to remain on the position of application for a long time since it tends to be dissolved in and lost to sweat or the like. In addition, the hydrophilic ointment base is not expected to protect the position of application from digestive fluids (aqueous solutions). That is, the ointment base absorbs digestive fluids to become decomposed, whereby the digestive fluids contact the skin, mucosa and tissue.

In the case of a large-intestinal fistula (artificial anus), skin surfaces can be contaminated by colon and other bacilli. For the same reason as above, the ointment applied to the skin adjacent this fistula is ineffective to protect the skin from contact with contents of the alimentary canal.

It is also difficult to obtain an ointment having a required viscosity with an ointment base consisting of boric acid and zine oxide or Azunol Ointment of Nippon Shinyaku Co. Such an ointment base is undesirable since it causes, as does the ointment having the Macrogol base, allergy and stimulation of mucosa or an affected part such as an eroded part or an ulcer which in particular requires safety.

In order to solve the foregoing problems, the present inventor has carried out intensive researches for years on the relationship between the safety of gabexate mesylate and the ointment base.

It has now been found that white vaseline is most desirable from the point of view of safety to the skin and the like, and that gabexate mesylate is stable in white vaseline. However, an ointment base consisting of white vaseline alone is too viscous for the ointment to be applied appropriately. There is thus a problem relating to its handling.

The inventor then prepared a gabexate mesylate ointment by adding gabexate mesylate and a viscosity controller to the base consisting of white vaseline. Further researches have been conducted on the stability of gabexate mesylate in this ointment base.

SUMMARY OF THE INVENTION

A primary object of the present invention is to provide an ointment with viscosity adjusted for improved handling, which is prepared by mixing gabexate mesylate with at least one type of viscosity controller selected from the group consisting of liquid paraffin, squalene and fatty acid ester containing 8-20 carbon atoms.

In order to achieve this object, a gabexate mesylate ointment according to the present invention comprises 0.01-8% by weight of gabexate mesylate, 25-80% by weight of white vaseline, and 20-75% by weight of at least one type of viscosity controller selected from the group consisting of liquid paraffin, squalene and fatty acid ester containing 8-20 carbon atoms.

To describe gabexate mesylate in greater detail, it is a compound expressed in the following structural formula:

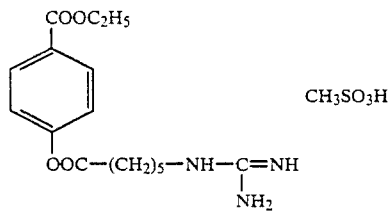

This substance is in the form of white crystal or crystalline powder highly insoluble in water.

Good results cannot be obtained where gabexate mesylate is added in too small an amount, i.e. less than 0.01% by weight. On the other hand, if gabexate mesylate exceeds 8% by weight, it will produce only a limited effect of treatment and is undesirable from the economic point of view as well. Thus gabexate mesylate should suitably be added in 0.1-5% by weight, preferably 0.1-2% by weight.

Where white vaseline is added in less than 25% by weight, the ointment base is too fluid and is difficult to fix to a position of application. On the other hand, its amount exceeding 80% by weight results in excessive viscosity which impairs its handling. From this point of view, white vaseline should be added in 30-75% by weight.

The present invention is not limited to any types of white vaseline, liquid paraffin, squalene and fatty acid ester containing 8-20 carbon atoms as long as these substances are suited for use as the ointment base.

In the present invention, the mixture of gabexate mesylate and white vaseline may be added with (1) liquid paraffin to control the ointment viscosity, (2) squalene to control the ointment viscosity, (3) fatty acid ester containing 8-20 carbon atoms to control the ointment viscosity, or (4) two or more of liquid paraffin, squalene and fatty acid ester containing 8-20 carbon atoms to control the ointment viscosity.

According to the present invention, the mixture of gabexate mesylate and white vaseline is added with at least one type of viscosity controller preferably in 20-75% by weight, which viscosity controller is selected from the group consisting of liquid paraffin, squalene and fatty acid ester containing 8-20 carbon atoms. Where the viscosity controller is added in too small an amount, i.e. less than 20% by weight, the ointment becomes too viscous and difficult to handle. Where the amount of the viscosity controller exceeds 75% by weight, the ointment becomes too fluid and difficult to fix to the position of application. Thus the viscosity controller should preferably be added in 30-70% by weight from the point of view of realizing an ointment which is easy to handle and fix to the position of application.

Another object of the present invention is to provide an ointment with improved stability of gabexate mesylate and further improved handling, which is prepared by mixing the foregoing ointment with at least one type of viscosity controlling auxiliary selected from the group consisting of higher alcohol and higher fatty acid containing 14-34 carbon atoms, beeswax and spermaceti wax.

In order to achieve this object, a gabexate mesylate ointment according to the present invention comprises 0.01-8% by weight of gabexate mesylate, 25-80% by weight of white vaseline, 20-75% by weight of at least one type of viscosity controller selected from the group consisting of liquid paraffin, squalene and fatty acid ester containing 8-20 carbon atoms, and 1-20% by weight of at least one type of viscosity controlling auxiliary selected from the group consisting of higher alcohol and higher fatty acid containing 14-34 carbon atoms, beeswax and spermaceti wax.

In other words, the second object of the present invention is achieved by further adding the viscosity controlling auxiliary.

The viscosity controlling auxiliary used in the the present invention is not limited to any particular type as long as the auxiliary is not stimulative to the skin or the like and improves the viscosity control and stability of the ointment.

The viscosity controlling auxiliary, preferably, comprises at least one type selected from the group consisting of higher alcohol and higher fatty acid containing 14-34 carbon atoms, beeswax and spermaceti wax.

The viscosity controlling auxiliary, preferably, is mixed in 1-20% by weight of the entire ointment. The viscosity controlling auxiliary mixed in less than 1% by weight produces little effect and is insignificant. On the other hand, where the amount of the auxiliary exceeds 20% by weight, the ointment will become too viscous which is undesirable. Taking these facts into account, the viscosity controlling auxiliary should preferably be added in 3-15% by weight.

How the present invention functions will be described in detail hereinafter.

The present invention provides the above composition, in which the hydrophobic ointment base is employed for improved stability of gabexate mesylate, and the viscosity controller such as liquid paraffin is used for adjusting the viscosity to an intended use. This ointment may suitably be used to sensitive locations such as mucosa, an eroded part, an ulcer and so on.

The hydropobic ointment base is effective to avoid direct contact between the skin, mucosa and tissue adjacent an abdominal outlet position of an alimentary canal fistula, particularly a pancreatic or small-intestinal fistula, and digestive fluids, typically pancreatic juice, containing protease.

Thus the ointment according to the present invention has a function to protect the skin, mucosa and tissue as well as a protease deactivating function of gabexate mesylate. Furthermore, gabexate mesylate is prevented from being lost through dissolution in digestive fluids, water content in the alimentary canal, sweat, body fluids and so on.

The skin adjacent a large-intestinal fistula (artificial anus) is protected from contact with contents of the alimentary canal including colon bacilli, thereby avoiding its inflammation due to contamination.

As will be understood from the foregoing description of the functions, the present invention provides the following advantages:

Since the composition according to the present invention includes a hydrophobic ointment base, the ointment may be stored for a long period with gabexate mesylate remaining stable. The ointment further includes the viscosity controller for adjusting the viscosity, and the ointment base not stimulative to the skin, mucosa and tissue. This ointment may, therefore, be used safely and effectively at sensitive locations such as mucosa, an eroded part, an ulcer and so on.

The hydrophobic ointment base is effective to avoid contact between the skin, mucosa and tissue adjacent the outlet position of an alimentary canal fistula and digestive fluids containing protease, thereby to prevent digestion and erosion of such locations. This feature assists in and further promotes the effect of the protease deactivating function of gabexate mesylate.

Further, the hydrophobic ointment base according to the present invention protects the skin and the like from direct contact with contents of the alimentary canal including colon bacilli, thereby avoiding its inflammation due to contamination.

This feature also minimizes the possibility of gabexate mesylate being lost through dissolution in digestive fluids, water content in the alimentary canal, sweat, body fluids and so on. Consequently, the ointment according to the invention maintains its efficacy over a long period of time.

Other objects and advantages of the present invention will be apparent from the following description of embodiments.

DETAILED DESCRIPTION OF THE EMBODIMENTS

The present invention will be described further with reference to embodiments but it should be understood that the invention is not limited to these embodiments.

Embodiments 1-30 [Table 1 (Parts 1 and 2)]

(A) Gabexate mesylate is placed in a mortar in the amounts shown in Table 1.

(B) The ointment base shown in Table 1 is preheated and melted, and then cooled to about 50° C. The base is placed little by little in the mortar to obtain the mixture ratios shown in Table 1. Thereafter the mixture is agitated in the mortar until it becomes semisolid, thereby to obtain gabexate mesylate ointments.

The numerical values in Table 1 are percentage by weight.

Comparative Examples 1-4 [Table 2]

Samples were obtained by using gabexate mesylate as in the embodiments and mixing it with the ointment base shown in Table 2.

The numerical values in Table 2 are also percentage by weight.

Tests were conducted to check the stability of gabexate mesylate in the ointments of the embodiments and comparative examples.

The ointments were stored in aluminum tubes at a temperature of 40° C. and at a relative humidity of 80%.

Test results are shown in Table 3.

The numerical values in Table 3 are percentage or indices of the gabexate mesylate content in the ointments after lapse of the stated numbers of days with reference to the gabexate mesylate content immediately following manufacture which is taken to be 100.

(A) Gabexate mesylate contents in the embodiments and comparative examples 1 and 2 were measured by the following method:

0.2 g of each product was accurately put into a separating funnel, the base was dispersed by adding 20 ml of n-hexane, and gabexate mesylate was extracted with 20 ml of acetonitrile. Further, an acetonitrile layer was washed with 20 ml of n-hexane. This operation was carried out twice. With all the acetonitrile layer removed, 0.2 ml of an internal standard solution (2 mg/ml acetonitrile solution of p-oxybenzoic acid and n-propyl) was added to distillate acetonitrile. After the distillation of acetonitrile, it was dissolved in 5 ml of acetonitrile again to form a sample solution.

Gabexate mesylate was measured on the basis of the sample solution by the HPLC method using a wavelength of 260 nm.

(B) Gabexate mesylate contents in comparative examples 3 and 4 were measured by the following method:

0.2 g of each product was taken accurately and was dissolved in 5 ml of acetonitrile and 0.2 ml of the internal standard solution was accurately added thereto to form a sample solution. This sample solution was measured by the operation as in (A) above.

From the results shown in Table 3, it will be seen that the ointments embodying the present invention have excellent stability of gabexate mesylate, are highly extendible, not soft and sticky, and fix to positions of application reliably.

The embodiments added with the viscosity controlling auxiliaries, like those without such addition, give an agreeable feeling to the skin without a stimulating sensation.

With comparative examples 1 and 2, gabexate mesylate shows good stability. However, these ointments are highly viscous and not very extendible, which is not satisfactory in terms of handling easiness.

Comparative examples 3 and 4 show very poor results with respect to the gabexate mesylate stability.

Further, 1 g of the ointment of each of the embodiments and comparative examples was immersed with filter paper (5 C Filter Paper manufactured by Toyo Roshi Co., Ltd., Japan) in artificial intestinal juice (1,000 ml of a mixture of 250 ml of an aqueous solution of 0.2M potassium dihydrogenphosphate, 118 ml of an aqueous solution of 0.2N sodium hydroxide, and water, which is manufactured by Toyo Roshi Co.), and was shelved at a temperature of 30° C. for 6 hours.

When the conditions were observed thereafter, the ointments embodying the present invention and those of comparative examples 1 and 2 were found remaining on the filter paper, whereas the ointments of comparative examples 3 and 4 had been dissolved and lost.

Further, the ointments were extracted with 100 ml of n-hexane from the filter paper having been shelved for 6 hours. The amount of gabexate mesylate in 20 ml of each ointment was measured by the same method as in Test (A). It was found that gabexate mesylate remained in 46.2–68.5% by weight of the theoretical value in the ointments embodying the present invention and those of comparative examples 1 and 2. In the case of comparative examples 3 and 4, no gabexate mesylate remained, having all been dissolved and lost.

The above results prove that the gabexate mesylate ointments having a hydrophobic base have the advantage of maintaining its effect on positions of application exposed to water content of the alimentary canal, sweat, body fluids and so on.

TABLE 1

(Part 1)

| | Gabexate Mesylate | White Vaseline | Liquid Paraffin | Squalene | Isopropyl myristate |
|---|---|---|---|---|---|
| Emb. 1 | 0.5 | 40 | 60 | — | — |
| Emb. 2 | 0.5 | 50 | 50 | — | — |
| Emb. 3 | 0.5 | 65 | 35 | — | — |
| Emb. 4 | 0.5 | 75 | — | 25 | — |
| Emb. 5 | 0.5 | 50 | 25 | 25 | — |
| Emb. 6 | 0.5 | 33 | 67 | — | — |
| Emb. 7 | 0.5 | 40 | 40 | 20 | — |
| Emb. 8 | 0.5 | 35 | 50 | 15 | 2 |
| Emb. 9 | 0.5 | 35 | 50 | 15 | — |
| Emb. 10 | 0.5 | 35 | 50 | 15 | 5 |
| Emb. 11 | 0.5 | 35 | 50 | 15 | 2 |
| Emb. 12 | 0.5 | 65 | — | 30 | — |
| Emb. 13 | 0.2 | 65 | — | 30 | — |
| Emb. 14 | 0.2 | 75 | — | 25 | — |
| Emb. 15 | 0.2 | 40 | 60 | — | — |
| Emb. 16 | 1 | 50 | 50 | 10 | — |
| Emb. 17 | 1 | 50 | 40 | 10 | 3 |
| Emb. 18 | 1 | 40 | 50 | 10 | 5 |
| Emb. 19 | 1 | 50 | 40 | 10 | — |
| Emb. 20 | 1 | 50 | 40 | 10 | 2 |
| Emb. 21 | 1.5 | 33 | 67 | 5 | — |
| Emb. 22 | 1.5 | 35 | 50 | 15 | 5 |
| Emb. 23 | 2 | 60 | 30 | — | 30 |
| Emb. 24 | 2 | 35 | 50 | 15 | 3 |
| Emb. 25 | 3 | 33 | 67 | — | — |
| Emb. 26 | 5 | 50 | 50 | — | — |
| Emb. 27 | 5 | 40 | 40 | 20 | 5 |
| Emb. 28 | 5 | 40 | 60 | — | — |
| Emb. 29 | 7 | 60 | — | — | 40 |
| Emb. 30 | 7 | 60 | — | — | 35 |

(Part 2)

| | Cetyl Alcohol | Stearic Acid | Beeswax | Spermaceti Wax |
|---|---|---|---|---|
| Emb. 1 | — | — | — | — |
| Emb. 2 | — | — | — | — |
| Emb. 3 | — | — | — | — |
| Emb. 4 | — | — | — | — |
| Emb. 5 | — | — | — | — |
| Emb. 6 | — | 5 | 5 | — |
| Emb. 7 | 2 | 5 | — | — |
| Emb. 8 | — | 5 | 2 | — |
| Emb. 9 | — | 5 | — | 5 |
| Emb. 10 | 5 | 5 | — | 5 |
| Emb. 11 | 2 | 3 | 3 | 5 |
| Emb. 12 | — | 5 | — | — |
| Emb. 13 | — | 5 | — | — |
| Emb. 14 | — | — | — | — |
| Emb. 15 | — | — | — | — |
| Emb. 16 | — | 5 | — | — |
| Emb. 17 | 5 | 3 | 2 | 2 |
| Emb. 18 | 3 | 5 | 2 | — |
| Emb. 19 | 5 | 5 | 5 | — |
| Emb. 20 | 2 | 2 | 5 | 2 |
| Emb. 21 | 5 | — | — | 10 |
| Emb. 22 | — | 5 | 5 | — |
| Emb. 23 | — | — | — | — |
| Emb. 24 | 2 | 3 | 3 | 5 |
| Emb. 25 | 5 | — | — | — |
| Emb. 26 | — | 5 | — | — |
| Emb. 27 | 2 | 5 | — | — |
| Emb. 28 | 2 | — | 10 | — |
| Emb. 29 | 5 | — | — | — |
| Emb. 30 | — | 5 | 5 | — |

TABLE 2

| | Gabexate Mesylate | White Vaseline | Stearic Acid | Macrogol 400 | Macrogol 600 |
|---|---|---|---|---|---|
| C. Ex 1 | 0.5 | 100 | — | — | — |
| C. Ex 2 | 0.5 | 100 | — | — | — |
| C. Ex 3 | 0.2 | — | — | 60 | 40 |
| C. Ex 4 | 0.2 | — | 5 | 60 | 35 |

TABLE 3

(Part 1)

| | After Manufact. | After 35 Days | After 70 Days | After 120 Days |
|---|---|---|---|---|
| Emb. 1 | 100 | 99.5 | 99.0 | 98.5 |
| Emb. 2 | 100 | 99.5 | 99.1 | 98.6 |
| Emb. 3 | 100 | 99.3 | 99.3 | 98.3 |
| Emb. 4 | 100 | 99.0 | 99.5 | 99.1 |
| Emb. 5 | 100 | 100 | 99.5 | 99.3 |
| Emb. 6 | 100 | 99.8 | 99.5 | 99.0 |
| Emb. 7 | 100 | 99.8 | 99.2 | 98.5 |
| Emb. 8 | 100 | 100 | 99.6 | 99.8 |
| Emb. 9 | 100 | 99.0 | 99.0 | 98.5 |
| Emb. 10 | 100 | 100 | 98.9 | 99.5 |
| Emb. 11 | 100 | 99.4 | 100 | 99.0 |
| Emb. 12 | 100 | 99.3 | 99.0 | 98.6 |
| Emb. 13 | 100 | 99.0 | 99.3 | 99.0 |
| Emb. 14 | 100 | 99.6 | 99.2 | 99.2 |
| Emb. 15 | 100 | 99.7 | 98.6 | 98.2 |
| Emb. 16 | 100 | 99.5 | 99.0 | 98.5 |
| Emb. 17 | 100 | 99.3 | 99.5 | 99.8 |
| Emb. 18 | 100 | 99.5 | 99.8 | 99.5 |
| Emb. 19 | 100 | 99.5 | 99.3 | 99.5 |
| Emb. 20 | 100 | 100 | 99.5 | 99.1 |
| Emb. 21 | 100 | 99.1 | 98.4 | 98.7 |
| Emb. 22 | 100 | 99.7 | 99.5 | 99.2 |
| Emb. 23 | 100 | 98.9 | 99.1 | 98.9 |
| Emb. 24 | 100 | 99.3 | 99.2 | 98.8 |
| Emb. 25 | 100 | 99.6 | 100 | 99.7 |
| Emb. 26 | 100 | 98.5 | 98.4 | 98.0 |
| Emb. 27 | 100 | 98.9 | 98.1 | 98.1 |
| Emb. 28 | 100 | 98.6 | 98.7 | 98.2 |
| Emb. 29 | 100 | 99.2 | 99.4 | 98.6 |
| Emb. 30 | 100 | 99.4 | 98.6 | 98.5 |
| C. Ex 1 | 100 | 97.5 | 94.5 | 91.5 |
| C. Ex 2 | 100 | 96.5 | 94.8 | 93.5 |
| C. Ex 3 | 100 | 87.2 | 81.5 | 75.5 |
| C. Ex 4 | 100 | 88.8 | 79.5 | 70.8 |

(Part 2)

| | After 165 Days | After 210 Days | After 240 Days | After 300 Days |
|---|---|---|---|---|
| Emb. 1 | 98.5 | 98.0 | 97.5 | 97.3 |

TABLE 3 -continued

| | | | | |
|---|---|---|---|---|
| Emb. 2 | 98.2 | 98.3 | 98.0 | 97.8 |
| Emb. 3 | 98.5 | 98.1 | 98.5 | 98.0 |
| Emb. 4 | 99.0 | 99.3 | 99.3 | 98.8 |
| Emb. 5 | 99.3 | 98.9 | 98.5 | 98.2 |
| Emb. 6 | 98.8 | 98.5 | 97.8 | 97.7 |
| Emb. 7 | 98.8 | 99.8 | 99.0 | 99.8 |
| Emb. 8 | 99.6 | 99.8 | 99.6 | 99.7 |
| Emb. 9 | 98.5 | 98.0 | 98.0 | 97.8 |
| Emb. 10 | 99.2 | 98.8 | 98.5 | 98.6 |
| Emb. 11 | 98.5 | 98.1 | 98.8 | 98.0 |
| Emb. 12 | 98.8 | 98.7 | 98.2 | 99.9 |
| Emb. 13 | 98.1 | 99.1 | 98.5 | 98.2 |
| Emb. 14 | 98.6 | 98.9 | 98.5 | 98.2 |
| Emb. 15 | 98.3 | 98.0 | 97.6 | 97.1 |
| Emb. 16 | 98.8 | 98.2 | 97.8 | 98.8 |
| Emb. 17 | 99.4 | 99.4 | 99.5 | 99.3 |
| Emb. 18 | 99.3 | 99.8 | 99.7 | 99.8 |
| Emb. 19 | 99.0 | 99.0 | 99.3 | 99.5 |
| Emb. 20 | 99.3 | 99.4 | 98.3 | 98.6 |
| Emb. 21 | 98.6 | 99.0 | 98.9 | 99.3 |
| Emb. 22 | 98.7 | 99.2 | 98.8 | 98.6 |
| Emb. 23 | 98.5 | 99.4 | 98.9 | 98.5 |
| Emb. 24 | 98.9 | 98.5 | 98.7 | 98.5 |
| Emb. 25 | 99.4 | 98.6 | 99.2 | 98.6 |
| Emb. 26 | 98.1 | 98.0 | 97.7 | 97.0 |
| Emb. 27 | 97.6 | 97.4 | 97.5 | 97.2 |
| Emb. 28 | 97.9 | 97.6 | 97.3 | 97.7 |
| Emb. 29 | 98.9 | 98.1 | 98.3 | 98.0 |
| Emb. 30 | 98.7 | 98.3 | 98.4 | 98.1 |
| C. Ex 1 | 88.0 | 88.5 | 88.0 | 89.9 |
| C. Ex 2 | 92.0 | 91.5 | 91.0 | 92.2 |
| C. Ex 3 | 62.9 | 52.5 | 45.5 | 37.4 |
| C. Ex 4 | 61.8 | 51.8 | 42.5 | 37.1 |

What is claimed is:

1. A gabexate mesylate ointment comprising 0.01-8% by weight of gabexate mesylate, 25-80% by weight of white vaseline, and 20-75% by weight of at least one viscosity controller selected from the group consisting of liquid paraffin, squalene and fatty acid ester containing 8-20 carbon atoms.

2. A gabexate mesylate ointment as claimed in claim 1, wherein gabexate mesylate is contained in 0.1-5% by weight.

3. A gabexate mesylate ointment as claimed in claim 2, wherein gabexate mesylate is contained in 0.1-2% by weight.

4. A gabexate mesylate ointment as claimed in claim 1, wherein white vaseline is contained in 30-75% by weight.

5. A gabexate mesylate ointment as claimed in claim 2, wherein white vaseline is contained in 30-75% by weight.

6. A gabexate mesylate ointment as claimed in claim 3, wherein white vaseline is contained in 30-75% by weight.

7. A gabexate mesylate ointment as claimed in claim 1, wherein the viscosity controller is contained in 30-70% by weight.

8. A gabexate mesylate ointment as claimed in claim 2, wherein the viscosity controller is contained in 30-70% by weight.

9. A gabexate mesylate ointment as claimed in claim 3, wherein the viscosity controller is contained in 30-70% by weight.

10. A gabexate mesylate ointment as claimed in claim 4, wherein the viscosity controller is contained in 30-70% by weight.

11. A gabexate mesylate ointment as claimed in claim 1, further comprising 1-20% by weight of at least one type of viscosity controlling auxiliary selected from the group consisting of higher alcohol and higher fatty acid containing 14-34 carbon atoms, beeswax and spermaceti wax.

12. A gabexate mesylate ointment as claimed in claim 11, wherein gabexate mesylate is contained in 0.1-5% by weight.

13. A gabexate mesylate ointment as claimed in claim 6, wherein gabexate mesylate is contained in 0.1-2% by weight.

14. A gabexate mesylate ointment as claimed in claim 11, wherein gabexate mesylate is contained in 0.1-2% by weight.

15. A gabexate mesylate ointment as claimed in claim 11, wherein white vaseline is contained in 30-75% by weight.

16. A gabexate mesylate ointment as claimed in claim 12, wherein white vaseline is contained in 30-75% by weight.

17. A gabexate mesylate ointment as claimed in claim 13, wherein white vaseline is contained in 30-75% by weight.

18. A gabexate mesylate ointment as claimed in claim 11, wherein the viscosity controller is contained in 30-70% by weight.

19. A gabexate mesylate ointment as claimed in claim 12, wherein the viscosity controller is contained in 30-70% by weight.

20. A gabexate mesylate ointment as claimed in claim 13, wherein the viscosity controller is contained in 30-70% by weight.

21. A gabexate mesylate ointment as claimed in claim 14, wherein the viscosity controller is contained in 30-70% by weight.

22. A gabexate mesylate ointment as claimed in claim 11, wherein the viscosity controlling auxiliary is contained in 3-15% by weight.

23. A gabexate mesylate ointment as claimed in claim 12, wherein the viscosity controlling auxiliary is contained in 3-15% by weight.

24. A gabexate mesylate ointment as claimed in claim 13, wherein the viscosity controlling auxiliary is contained in 3-15% by weight.

25. A gabexate mesylate ointment as claimed in claim 14, wherein the viscosity controlling auxiliary is contained in 3-15% by weight.

26. A gabexate mesylate ointment as claimed in claim 15, wherein the viscosity controlling auxiliary is contained in 3-15% by weight.

* * * * *